United States Patent
Li et al.

(10) Patent No.: US 7,829,148 B2
(45) Date of Patent: Nov. 9, 2010

(54) COATING PROCESS TO PRODUCE CONTROLLED RELEASE COATINGS

(75) Inventors: Jian-Xin Li, North Brunswick, NJ (US); Brian A. C. Carlin, Pittsgrove, NJ (US)

(73) Assignee: FMC Corporation, Philadelphia, PA (US)

( * ) Notice: Subject to any disclaimer, the term of this patent is extended or adjusted under 35 U.S.C. 154(b) by 480 days.

(21) Appl. No.: 11/669,748

(22) Filed: Jan. 31, 2007

(65) Prior Publication Data

US 2007/0184198 A1    Aug. 9, 2007

Related U.S. Application Data

(60) Provisional application No. 60/832,364, filed on Jul. 21, 2006, provisional application No. 60/765,858, filed on Feb. 7, 2006.

(51) Int. Cl.
*B05D 3/02* (2006.01)
(52) U.S. Cl. .................... 427/385.5; 427/384
(58) Field of Classification Search ............ 427/385.5, 427/384
See application file for complete search history.

(56) References Cited

U.S. PATENT DOCUMENTS

| | | | |
|---|---|---|---|
| 4,318,944 A * | 3/1982 | Hall ............................ 427/377 |
| 4,330,338 A | 5/1982 | Banker |
| 4,462,839 A | 7/1984 | McGinley |
| 4,562,098 A | 12/1985 | Ahmed |
| 4,600,645 A | 7/1986 | Ghebre-Sellassie et al. |
| 5,273,760 A | 12/1993 | Oshlack et al. |
| 5,286,493 A | 2/1994 | Oshlack et al. |
| 5,326,572 A | 7/1994 | Mehra et al. |
| 5,472,712 A | 12/1995 | Oshlack et al. |
| 5,500,227 A | 3/1996 | Oshlack et al. |
| 5,580,578 A | 12/1996 | Oshlack et al. |
| 5,639,476 A | 6/1997 | Oshlack et al. |
| 5,681,585 A | 10/1997 | Oshlack et al. |
| 6,129,933 A | 10/2000 | Oshlack et al. |

(Continued)

FOREIGN PATENT DOCUMENTS

JP    1997-194347    7/1997

OTHER PUBLICATIONS

BASF Press Release, "BASF Extends Kollicoat IR Range," Dec. 13, 2004.

(Continued)

*Primary Examiner*—Michael Barr
*Assistant Examiner*—Robert S Walters, Jr.

(57) ABSTRACT

An aqueous polymer coating composition containing at least one latex or pseudolatex is coated on a substrate in a high humidity coating process followed by heat treatment of the coated substrate above the film forming temperature of the coating at low humidity. The coated substrate gives a stable reproducible dissolution profile substantially insensitive to temperature or humidity conditions upon storage. The high humidity coating process is achieved by addition of water to the coating chamber through dilution of the coating formulation or humidification of inlet air. Contrary to the conventional low humidity coating process, residual water is retained in the coating layer of the coated substrates in the coating step. When the coated substrates are heat treated at a temperature greater than the minimum film forming temperature, the residual water in the coating layer will ensure adequate capillary force for the completion of film coalescence. High humidity heat treatment is not needed.

28 Claims, 2 Drawing Sheets

U.S. PATENT DOCUMENTS

| | | | |
|---|---|---|---|
| 6,143,353 | A | 11/2000 | Oshlack et al. |
| 6,316,031 | B1 | 11/2001 | Oshlack et al. |
| 6,733,783 | B2 * | 5/2004 | Oshlack et al. ............. 424/473 |
| 6,905,709 | B2 | 6/2005 | Oshlack et al. |
| 7,070,806 | B2 | 7/2006 | Oshlack et al. |
| 2003/0175342 | A1 | 9/2003 | Kolter et al. |
| 2003/0232122 | A1 * | 12/2003 | Chappa et al. ............... 427/2.1 |
| 2004/0228917 | A1 | 11/2004 | Oshlack et al. |
| 2006/0269605 | A1 | 11/2006 | Lizio et al. |

OTHER PUBLICATIONS

Lange, Ronald F.M. et al., "The Development of an Instant Release Tablet Coating," International Pharmaceutical Excipients Council Europe News, May 2004.

Rohera, Ghagwan D. and Parikh, Nilesh H., "Influence of Type and Level of Water-Soluble Additives on Drug Release and Surface and Mechnical Properties of Surelease(R) Films," Pharmaceutical Development and Technology, 2002, pp. 421-432, vol. 7, No. 4.

Kollicoat(R) IR, Technical Information Bulletin, Jul. 2006.

Kollicoat(R) SR 30 D, Technical Information Bulletin, Aug. 2005.

Mies, S. et al., "Correlation of Drug Permeation Through Isolated Films and Coated Dosage Forms Based on Kollicoat(R) SR 30 D/IR," AAPS Annual Meeting and Exposition, Nov. 7-11, 2004, Baltimore, Maryland.

Kolter, K. and Ruchatz, F., "Kollicoat(R) SR 30 D—A New Sustained Release Excipient," The 26th International Symposium on Controlled Release of Bioactive Materials, Jun. 20-25, 1999, Boston, MA.

Bordaweker, M., Zia, H., and Quadir, A., "Release Characteristics of Selected Drugs with a Newly Developed Polyvinyl Acetate Dispersion," 31st International Symposium on Controlled Release of Bioactive Material, Jun. 12-16, 2004, Honolulu, Hawaii.

Meyer, K. and Kolter, K., "Reliability of Drug Release from an Innovative Single Unit Kollicoat(R) Drug Delivery System," 31st International Symposium on Controlled Release of Bioactive Materials, Jun. 12-16, 2004, Honolulu, Hawaii.

Postel, M. et al., Innovative Tilidine-Naloxone Sustained Release Drug Delivery Systems based on Kollicoat(R) Polymers, Poster, May 21, 2004.

International Search Report & Written Opinion—PCT/US2007/061385—International Filing Date Jan. 31, 2007.

* cited by examiner

COATING PROCESS TO PRODUCE CONTROLLED RELEASE COATINGS

BACKGROUND OF THE INVENTION

1. Field of the Invention

The present invention relates to coating processes used to produce controlled-release coatings and to products made by the process.

2. Brief Description of the Prior Art

Controlled release dosage forms are designed to provide prolonged pharmacological action after the administration of the dosage form, as compared with the administration of an immediate release dosage form. Such sustained response offers many inherent therapeutic benefits that cannot be obtained with immediate release and short acting products.

Controlled release dosage forms known in the art include coated beads, pellets or spheroids, coated capsules, coated tablets and ion exchange resins, wherein the sustained release of the active drug is realized via permeation of the active drug through a coating layer or a matrix formulation to slow down the release of the drug.

An essential characteristic of all controlled release dosage forms is the stability of the dosage forms. The stability of a pharmaceutical dosage form refers to the constancy of its physical, chemical, microbiological, therapeutic, pharmaceutical, and toxicological properties during storage in a specific container under a specific set of conditions. Stability studies are required by Good Manufacturing Practices (GMPs), the U.S.P., as well as New Drug Applications (NDAs) and Investigational New Drug Applications (INDs).

Hydrophobic polymers have been used as a film former to coat tablets, capsules, suppositories, spheroids, beads or microspheres to develop controlled release dosage forms. It is known in the prior art that these hydrophobic coatings are formulated in the form of an organic solution, pseudolatex or suspension. Since most of these polymers are insoluble in water, a polymer solution in an organic solvent is sprayed onto the individual drug forms (such as beads or tablets) and the solvent is evaporated during the coating process. However, the evaporated solvent poses environmental pollution concerns. In addition, coating formulations with organic solvents have inherent problems with regard to flammability, carcinogenicity, and safety.

For these reasons, it is desirable to use an aqueous polymer coating composition based on a latex or pseudolatex of an insoluble polymer to prepare a controlled release formulation. However the stability of coated substrates prepared using these aqueous polymer coating compositions remains a challenge. In particular, it is known that the drug release profile changes upon storage of the coated substrates. Such instability is not found when the coating is formulated by dissolution of the polymer composition in an organic solvent.

SUMMARY OF THE INVENTION

In one aspect, the present invention is directed to a process for coating a substrate with an aqueous polymer coating composition containing at least one latex or pseudolatex by: (1) coating the substrate with the aqueous polymer coating composition under high relative humidity conditions followed by: (2) a heat treatment step conducted under low humidity conditions. In one embodiment, the high humidity coating process is conducted at a relative humidity greater than 40%. In another embodiment, the heat treatment step is conducted at a low humidity of less than 16 grams of water per kg of air.

In another embodiment, the coated substrate produced by this process has superior barrier properties to a coated substrate made from the same coating composition and substrate prepared under low humidity coating and low humidity curing conditions.

In another embodiment, the coated substrate produced by this process has a superior stability of the release profile over a period of up to three years under normal storage conditions compared to a coated substrate of the same coating composition and substrate prepared under low humidity coating and low humidity curing conditions.

In another embodiment, the coated substrate produced by this process has a lower diffusivity as compared to a coated substrate of the same coating composition and substrate prepared under low humidity coating and low humidity curing conditions.

In another embodiment, the coated substrate produced by this process requires a lower film thickness to achieve a desired release profile as compared to a coated substrate of the same coating composition and substrate prepared under low humidity coating and low humidity curing conditions.

DETAILED DESCRIPTION OF THE PREFERRED EMBODIMENTS

Figure 1:
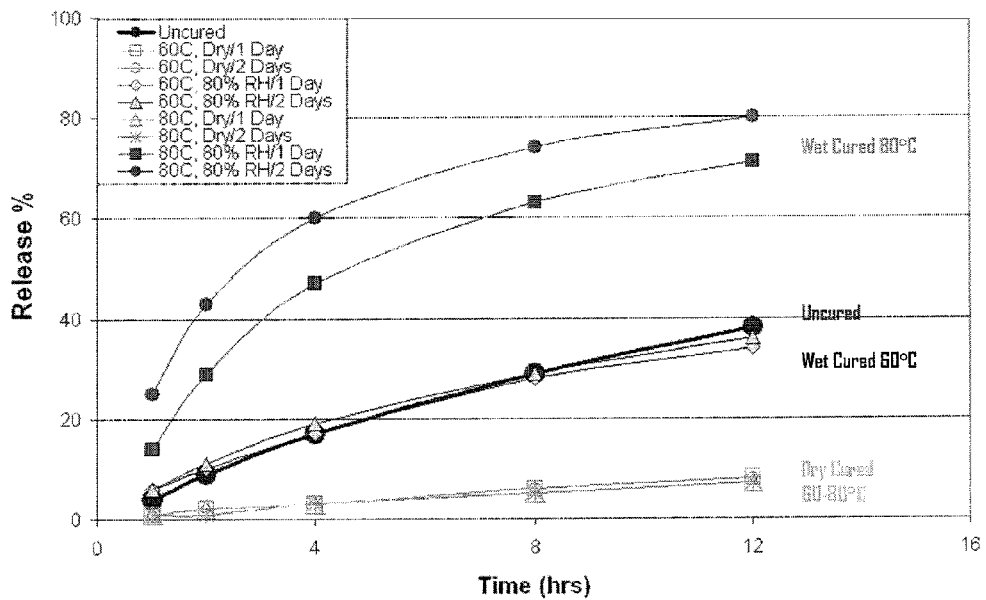
FIG. 1 shows the effect of curing conditions on theophylline release from coated pellets (high humidity coating, 4% coating weight gain).

Many polymers have been investigated for use in coating substrates, such as pellets, tablets, capsules, powders, granules, beads, and films. Most coated substrates are prepared by deposition of coating compositions made up of one or more film-forming polymers resulting in films that usually represent about 1 to 150% by weight, based on the weight of the coated substrate in the final coated product. The characteristics of the polymer used in forming the film are governed by the polymer's structure, size, and properties including mechanical, chemical and barrier properties. Common film-formers e.g. those used in pharmaceutical applications, include soluble polymers, such as alginates, carrageenans, hydroxypropyl methylcellulose, methyl hydroxyethylcellulose, hydroxypropylcellulose, sodium carboxymethylcellulose, soluble acrylate and methacylate copolymers, and others, as well as dispersions of insoluble polymers, in the form of lattices and pseudolaftices, such as ethylcellulose, insoluble acrylate and methacrylate copolymers, water insoluble cellulosics, cellulose acetate, cellulose acetate phthalate, and others.

The present invention is directed towards a process for coating a substrate with aqueous polymer coating compositions having therein a latex or pseudolatex under high humidity conditions, followed by a heat treatment step to coalesce a film under low humidity conditions. Substrates, e.g. pellets, tablets, capsules, powders, granules, beads, and films used in the present invention typically contain an active agent, e.g., a pharmaceutically active agent. The coated substrates produced by the process of the present invention have a stable moisture-resistant film that has a lower diffusivity with superior barrier properties compared to coated substrates prepared under low humidity coating and curing conditions, and provide a superior, stable release profile under normal storage conditions for up to three years. Moisture-resistant films produced by the present invention act as a controlled release layer to allow release of the active agent from the coated substrate in a controlled manner over time. As used herein, "latex or pseudolatex film formers" refers to that group of polymers that, when finely divided in aqueous dispersion, are capable of coalescing to form a coherent film. Latex or pseudolatex film formers of the present invention include dispersions of insoluble polymers, such as ethylcellulose, acrylate and methacrylate copolymers, water insoluble cellulosics, cellulose acetate, cellulose acetate phthalate, and others. Suitable aqueous polymer coating compositions may comprise at least one of ethylcellulose, methacrylate copolymers, acrylate copolymers, water insoluble cellulosics, cellulose acetate phthalate, polymer latexes such as EUDRAGIT® polymer, SURELEASE® polymer latex and SURETERIC® polymer latex, cellulose acetate trimellitate, polyvinyl acetate phthalate, hydroxypropylmethylcellulose phthalate, hydroxypropylmethylcellulose acetate succinate, polylactide or silicone elastomer latex.

In this invention, coated substrates are prepared by deposition of aqueous polymer coating compositions of one or more latex or pseudolatex film-forming polymers resulting in films that generally have a thickness of from about 5 microns to about 100 microns. Generally the thickness of the formed film should be 5 microns or greater. Films less than 5 microns thick may have insufficient film strength and integrity and this may cause the film properties to change over time. Although there is no specific upper limit, when the film is too thick, the coating process takes a long time, which is not practical. In terms of such a restriction, the upper limit for the coating thickness is approximately 100 microns. When the film becomes thicker, the release rate may be excessively slowed. In such a case, a suitable water-soluble substance may be included in the aqueous coating composition as a pore former and the suitability of the release rate and film thickness should be confirmed. The amount of coating varies greatly depending on the particle size and shape of the uncoated substrate, as well as the smoothness of its surface. However, it should be on the order of 1 to 150 parts by weight, and, preferably, on the order of 1 to 50 parts by weight, per 100 parts by weight of the uncoated substrate.

A preferred film former for use in the controlled release coatings is ethylcellulose. Ethylcellulose, a cellulose ether that is formed by the reaction of ethyl chloride with alkaline cellulose, is completely insoluble in water and gastrointestinal juices. Because ethylcellulose has a relatively high glass transition temperature, it does not form flexible films under normal coating conditions, and thus it is necessary to plasticize the ethylcellulose in the coating composition.

One commercially-available aqueous dispersion of ethylcellulose is AQUACOAT® ECD (FMC Corp., Philadelphia, Pa., U.S.A.). AQUACOAT® ECD ethylcellulose dispersion is prepared by dissolving the ethylcellulose in a water-immiscible organic solvent and then emulsifying the same in water in the presence of a surfactant and a stabilizer. After homogenization to generate submicron droplets, the organic solvent is evaporated under vacuum to form a pseudolatex. The plasticizer is not incorporated in the pseudolatex during the manufacturing phase. Thus, prior to using the same as a coating, it is necessary to intimately mix the AQUACOAT® ECD ethylcellulose dispersion with a suitable plasticizer. Plasticizer can be readily incorporated into the AQUACOAT® ECD ethylcellulose dispersion by stirring using a propeller-type mixing blade.

It is essential that the latex or pseudolatex particles do not aggregate, flocculate or coagulate in the dispersion prior to or during application, e.g., by spraying or fluidization onto the substrate, as loosely-packed or adherent particles resistant to capillary forces disrupt the mechanism of film formation which relies upon close packing of the particles on the substrate surface followed by sintering or coalescing into a coherent film.

It is preferred that the aqueous polymer coating composition used in the present invention include an effective amount of a suitable plasticizer, as it has been found that the use of a plasticizer with a latex or pseudolatex will further improve the physical properties of the film. The plasticization may be accomplished by either so-called "internal plasticization" or "external plasticization." Internal plasticization usually pertains directly to molecular modifications of the polymer during its manufacture, e.g., by copolymerization, such as altering and/or substituting functional groups, controlling the number of side chains, or controlling the length of the polymer. Such techniques are usually not performed by the formulator of the coating solution, but rather during the design of the polymer latex.

External plasticization involves the addition of a material to a film solution so that the requisite changes in film properties of the dry film can be achieved.

The suitability of a plasticizer depends on its affinity or solvating power for the polymer and its effectiveness at interfering with polymer-polymer attachments. Such activity imparts the desired flexibility by relieving molecular rigidity. Generally, the amount of plasticizer included in a coating composition is based on the concentration of the film-former, e.g., most often from about 1 to about 50 percent by weight of the film-former. Selection of the appropriate type and/or level of plasticizer may also prevent negative film properties such as tackiness or film property changes over time e.g. surface bloom. The preferred concentration of the plasticizer can be determined and optimized with the latex or pseudolatex in the aqueous coating composition considering the processing conditions and required film properties.

An important parameter in the determination of a suitable plasticizer for a polymer is related to the glass transition temperature (Tg) of the polymer. The glass transition temperature is related to the temperature or temperature range at which there is a fundamental change in the physical properties of the polymer. This change does not reflect a change in state, but rather a change in the macromolecular mobility of the polymer. Below the Tg, the polymer chain mobility is severely restricted. Thus, for a given polymer, if its Tg is above room temperature, the polymer will behave as a glass at room temperature, being hard, non-pliable and rather brittle, properties which could be somewhat restrictive in film coating since the coated dosage form may be subjected to a certain amount of external stress.

Incorporation of suitable plasticizers into the polymer matrix effectively reduces the Tg, so that films formed at a suitable film forming temperature are softer, more ductile and at use conditions such as room temperature are tougher, and may have an increased strength at failure, and thus are better able to resist mechanical stress. Other aspects of suitable plasticizers include the ability of the plasticizer to act as a good "swelling agent" for the lattice or pseudolattice, and the insolubility of the plasticizer in water.

Examples of suitable plasticizers include water insoluble plasticizers such as dibutyl sebacate, diethyl phthalate, triethyl citrate, tibutyl citrate, and triacetin, although it is possible that other water-insoluble plasticizers (such as acetylated monoglycerides, phthalate esters, castor oil, etc.) may be used. Triethyl citrate is an especially preferred plasticizer for aqueous dispersions of ethyl cellulose.

During mixing of the plasticizer and AQUACOAT® ECD ethylcellulose dispersion, plasticization of the pseudolatex particles will take place. Both the pseudolatex particles and plasticizer droplets are suspended in the water. The plasticization process involves the dissolution of the plasticizer into the aqueous phase, and the partition and diffusion of the plasticizer into the pseudolatex particles.

The coated substrates prepared by the process of the present invention slowly release the therapeutically active agent, e.g., when ingested and exposed to gastric fluids, and then to intestinal fluids. The controlled release profile of such coated substrates can be altered by means known in the art, for example, by varying the applied film thickness, altering the manner in which the plasticizer is added to the latex or pseudolatex, by varying the amount of plasticizer relative to the amount of latex or pseudolatex, by the inclusion of additional ingredients e.g. pore formers or excipients, by altering the time and temperature of the heat treatment relative to the film forming temperature, etc.

After the coating is applied to the surface, the pseudolatex particles will reach a closely packed arrangement on the coated surface due to the evaporation of water, driven by interfacial tension. There is a contracting force due to the existence of capillary water in the particle interstices. According to G. L. Brown, "Formation of films from polymer dispersions," *Journal of Polymer Science*, (1956) Vol. 22, pp. 423-434, the force is exerted in a direction normal to the water-particle interface, and it is the driving force for particle deformation. If the particles are too rigid to be deformed, water will evaporate, wetting of the particles is lost, and the driving force will disappear. The particles will remain rigid when the coating temperature is too low, or when the plasticization of polymer particle is inadequate. So it is important to add a sufficient amount of plasticizer to the coating formulation and to ensure that the coating temperature is above the glass transition temperature of the coating.

Important to the present invention is the formation of the controlled release film. A continuous film of aqueous polymer coating composition may be formed through a process known as gradual coalescence wherein the individual latex or pseudolatex particles coalesce to form a continuous film. The mechanism is distinct from simple deposition of solvent-based (soluble) polymer coatings. Water evaporation concentrates the insoluble nanosized latex or pseudolatex particles into a closely packed arrangement on the substrate surface. The capillary force of the interstitial water deforms the plasticized particles which will coalesce, or fuse together, at a temperature above the minimum film forming temperature to give a dense, continuous, and ductile film. Capillary force, as the driving force for particle coalescence, is necessary for film formation. If the humidity is low, however, water in the coating can evaporate quickly which shortens the action of capillary force. Since the deformation of polymer particles is time dependent, prolonged action of capillary force is beneficial to particle coalescence and film formation.

Higher coating temperatures, or an elevated temperature heat treatment ("curing") step, will tend to accelerate the process by promoting a faster rate of sintering of fused particles. However, if the coalescing process is not completed, it will lead to variability in release rates. It is important to avoid overdrying during coalescence and film formation. Prior art teachings use heat treatment in a high humidity environment to avoid overdrying. The present invention recognizes that a high capillary force can also be maintained by use of high humidity during the coating process, e.g. greater than 40% in the coating step, followed by a low humidity heat treatment step, e.g. less than 55% relative humidity in the drying step. Suitable high humidity conditions for the coating step are, for example, greater than 40% relative humidity, greater than 50% relative humidity, greater than 60% relative humidity, greater than 70% relative humidity, greater than 80% relative humidity, or greater than 90% relative humidity, so long as the pellets do not aggregate. Suitable low humidity conditions for the heat treatment step are, for example, less than 16 grams of water/kg of air, less than 10 grams of water/kg air, less than 8 grams of water/kg air, less than 5 grams of water per kg of air or less than 3 grams of water per kg of air so long as overdrying is avoided. The air flow, temperature, and relative volume of moisture to be removed will guide selection of the appropriate low humidity conditions for heat treatment step. For example, use of a fluidized bed requires a higher humidity of the inlet air stream to avoid overdrying. After coalescence, the film properties are said to remain constant.

In addition to plasticization and coating process, curing of the coated pellets/tablets may also affect the drug release profile. In order to obtain a controlled release formulation, it is usually necessary to coat the substrate comprising the therapeutically active agent with a sufficient amount of the aqueous dispersion of aqueous polymer coating composition to obtain a weight gain level of from about 1 to about 20 percent, preferably, from about 1 to about 5 percent, although the weight gain due to coating may be lesser or greater depending upon the physical properties of the therapeutically active agent, the desired release rate, the amount and type of plasticizer or other optional additives, including soluble polymer, colorants and the like, and the manner of incorporation of the same, for example. The coating formulations of the present invention should be capable of producing a strong, continuous film after heat treatment that is smooth and elegant, capable of supporting pigments and other coating additives, non-toxic, inert, and tack-free.

An example of a suitable controlled release profile pursuant to the present invention will provide a dissolution rate of the dosage form in vitro, when measured by the USP Paddle Method at 100 rpm in 900 ml aqueous buffer (pH between 1.6 and 7.2) at 37° C., of between 12.5 and 42.5% (by weight) of therapeutically active agent released after 1 hour, between 25 and 55% (by weight) released after 2 hours, between 45 and 75% (by weight) released after 4 hours, between 55 and 85% (by weight) released after 6 hours and between 65 and 95% (by weight) released after 8 hours. This example is, of course, not intended to be limiting in any manner whatsoever.

The coated substrates produced by the coating process of the present invention may include a wide variety of substrates, such as pellets, tablets, soft capsules, hard capsules, powders, granules, beads, films and film-enrobed dosage forms, microspheres, seeds, ion-exchange resin beads, and other multi-particulate systems, in order to obtain a desired controlled release of the therapeutically active agent. Granules, spheroids, or pellets, etc., prepared in accordance with the present invention can be presented in a capsule or film-enrobed dosage form or in any other suitable dosage form. They can be mixed with other drug preparations, or they can be mixed with other vehicles and drugs or particles that contain drugs or particles that have been subjected to film coating, after which they can be made into tablets or pills. They can also be mixed with food products or canned foods and administered as drugs. In addition to uses for medicinal drug products, they can also be used for agricultural chemicals, fertilizers or industrial applications.

A wide variety of therapeutically active agents can be used in conjunction with the present invention. The therapeutically active agents (e.g. pharmaceutical agents) which may be used in the compositions of the present invention include both water soluble and water insoluble drugs. Examples of such therapeutically active agents include antihistamines (e.g., dimenhydrinate, diphenhydramine, chlorpheniramine and dexchlorpheniramine maleate), analgesics (e.g., aspirin, codeine, morphine, dihydromorphone, oxycodone, etc.), anti-inflammatory agents (e.g., naproxyn, diclofenac, indomethacin, ibuprofen, acetaminophen, aspirin, sulindac), gastro-intestinals and anti-emetics (e.g., metoclopramide), anti-epileptics (e.g., phenytoin, meprobamate and nitrezepam), vasodilators (e.g., nifedipine, papaverine, diltiazem and nicardirine), anti-tussive, agents and expectorants (e.g., codeine phosphate), anti-asthmatics (e.g. theophylline), anti-spasmodics (e.g. atropine, scopolamine), hormones (e.g., insulin, leparin), diuretics (e.g., eltacrymic acid, bendrofluazide), anti-hypotensives (e.g., propranolol, clonidine), bronchodilators (e.g., albuterol), anti-inflammatory steroids (e.g., hydrocortisone, triamcinolone, prednisone), antibiotics (e.g., tetracycline), antihemorrhoidals, hypnotics, psychotropics, antidiarrheals, mucolytics, sedatives, decongestants, laxatives, antacids, vitamins, stimulants (including appetite suppressants such as phenylpropanolamine). The above list is not meant to be exclusive.

In certain preferred embodiments, the therapeutically active agent comprises hydromorphone, oxycodone, dihydrocodeine, codeine, dihydromorphine, morphine, buprenorphine, salts of any of the foregoing, and mixtures of any of the foregoing, and the like. In one preferred embodiment, the therapeutically active agent comprises aspirin, ibuprofen, or acetaminophen and their mixtures with other pharmaceutically compatible, therapeutically active agents.

When the controlled release coating of the present invention is to be applied to tablets, the tablet core (e.g. the substrate) may comprise the active agent along with any pharmaceutically accepted inert pharmaceutical filler (diluent) material, including, but not limited to, sucrose, dextrose, lactose, microcrystalline cellulose, xylitol, fructose, sorbitol, mixtures thereof and the like. Also, an effective amount of any generally accepted pharmaceutical lubricant, including calcium or magnesium soaps may be added to the above-mentioned ingredients of the excipient prior to compression of the tablet core ingredients. Most preferred is magnesium stearate in an amount of about 0.5-3% by weight of the solid dosage form.

The aqueous polymer coating compositions of the present invention preferably contain, in addition to the film-former, plasticizer, and solvent system (i.e., water), a colorant to provide elegance and product distinction. Color may be added to the solution of the therapeutically active agent instead of, or in addition to, the aqueous polymer coating composition. For example, color may be added to AQUA-COAT® ECD ethylcellulose dispersion via the use of alcohol or propylene glycol based color dispersions, milled aluminum lakes and opacifiers such as titanium dioxide, by adding color with shear to a water soluble polymer solution and then using low shear when adding to the plasticized AQUA-COAT® ECD ethylcellulose dispersion. Alternatively, any suitable method of providing color to the formulations of the present invention may be used.

The aqueous polymer coating composition comprising a latex or pseudolatex film former may be applied onto the substrate by spraying using any suitable spray equipment known in the art. The coating process is conducted under high relative humidity conditions, preferably at least 40% relative humidity at the substrate surface. The relative humidity during the coating process can be greater than 50% relative humidity, greater than 60% relative humidity, greater than 70% relative humidity, greater than 80% relative humidity or greater than 90% relative humidity. The high relative humidity condition in the coating process can be achieved by any appropriate means, e.g., by spraying an aqueous solution into a coating chamber or by diluting the aqueous polymer coating composition with an aqueous solution and/or by addition of water to the process air e.g. by spraying water or humidification to retard the rate of evaporation. The relative humidity should not be so high that moisture condenses on the substrate surface. While not being bound by theory, it is believed that the high relative humidity facilitates the formation of a uniform dense green (uncured) film structure on the substrate by providing sufficient time for close packing of the latex or pseudolatex particles applied during the coating step.

Preferably, a sufficient amount of the aqueous polymer coating composition to obtain a predetermined controlled release of said therapeutically active agent when said coated substrate is exposed to aqueous solutions, e.g. gastric fluid, is applied, taking into account the physical characteristics of the therapeutically active agent, the manner of incorporation of the plasticizer, etc.

After coating with, for example, a plasticized AQUA-COAT® ECD ethylcellulose dispersion coating composition, an additional overcoat of a film-former, such as LUSTRE-CLEAR® immediate release coating, is optionally applied to the beads. This overcoat is provided, if at all, in order to substantially reduce agglomeration of the beads, or to improve organoleptic or sensory functionality.

After completion of the coating step, the coated substrate receives a heat treatment step ("curing") in order to obtain a stabilized release rate of the therapeutically active agent. The temperature of the heat treatment step must be above the minimum film forming temperature but is limited at the upper end by the thermal stability of the substrate and its components, e.g. the therapeutically active agent. The heat treatment conditions are sufficient for the coated substrate to attain a dissolution profile which is substantially unaffected by further exposure to storage conditions of elevated temperature and/or humidity. In preferred embodiments of the present invention, the stabilized product is obtained by subjecting the coated substrate to oven curing at an elevated temperature for the required time period, with optimum values for temperature and time for the particular formulation being determined experimentally in the processing equipment. The heat treatment step may be carried out in conventional equipment e.g. an oven dryer, a fluidized bed, or in a coating pan.

An important aspect of the present invention is to facilitate the controlled formation of the film by allowing the capillary forces caused by moisture in the coating to facilitate coalescence. Heat treatment, for example, may be in an oven at 2-60° C. above the minimum film-forming temperature for anywhere from 1 to 48 hours. For example, standard curing at 60° C. will stabilize the dissolution profile of AQUACOAT® ECD ethyl-cellulose dispersion-containing pseudolatex formulation plasticized with triethyl citrate (to a minimum film forming temperature of about 40° C.), as will be demonstrated by the examples set forth herein. One skilled in the art will recognize that the time, temperature and humidity used in the heat treatment step will be dependent upon, and will need to be optimized for, the specific aqueous polymer coating composition used. It is within the scope of the present invention to use a controlled temperature in the heat treatment step, if desired, e.g. start at a lower temperature and increase the temperature during the heat treatment step.

EXAMPLES

The following examples illustrate various aspects of the present invention. They are not to be construed to limit the claims in any manner whatsoever. All parts are by weight and all temperatures are in degrees centigrade unless otherwise indicated.

Example 1

This example uses a dispersion with 15% solids and provides 4.0% weight gain due to coating, coated under high humidity conditions. Portions of the coated pellets were heat treated under different conditions and the data for heat treatment of the present invention under dry conditions are compared with data for a comparative heat treatment under high humidity.

An aqueous coating solution of 15% solids was prepared according to the formulation in Table 1. An aqueous coating dispersion of plasticized ethyl cellulose pseudo-lattices was prepared using the formulation in Table 1 by: (1) adding triethyl citrate to AQUACOAT® ECD-30 ethylcellulose dispersion (FMC Corp., Philadelphia Pa.) and mixing for one hour at a slow speed of approximately 100 to 150 RPM using a propeller mixer with a 3 inch impeller blade, and (2) adding deionized water and mixing for an additional 10 minutes.

TABLE 1

Coating formulation at 15% solids

| Ingredient | Weight (%) | Weight (%) of solids |
|---|---|---|
| AQUACOAT ECD-30 ethylcellulose dispersion | 40 | 80 |
| triethyl citrate | 3 | 20 |
| deionized water | 57 | 0 |
|  | 100 | 100 |

The coating dispersion was applied to an 800 gram batch size of theophylline pellets (average pellet size 1000 microns, 70% theophylline) according to the coating conditions in Table 2. The coating was conducted in a Niro Fluid Bed Dryer MP-1 with a Wurster column to a weight gain of 4% under high humidity conditions. The coating dispersion was stirred by a magnetic stirrer during spray application. The spray rate was measured by timed decrement of the coating removed from the coating vessel after initially zeroing on a Mettler balance.

TABLE 2

Coating conditions with Niro Fluid Bed Dryer MP-1 with Wurster Column

| Inlet Temperature | 60° C. |
|---|---|
| Air Flow | 60 m³/hr |
| Atomization Pressure | 1 Bar |
| Spray Rate | Masterflex Pump speed setting 15 |
| % RH in Bowl | High humidity: chiller and humidifier on |
| Weight Gain | 4.0% |
| Coating time | 20 minutes |

The coated pellets were divided and heat treated in a closed oven without air circulation under four different conditions:
1) 60° C. Dry
2) 80° C. Dry
3) 60° C. 80% Relative Humidity (RH)
4) 80° C. 80% Relative Humidity (RH)

The dry humidity samples were dried in an open container without active humidity control in a closed oven. The 80% humidity samples were oven dried in a closed container where the humidity was controlled using a saturated salt solution (KCl). Data for pellets cured under dry conditions are reported in Tables 3 and 4 and illustrate the present invention. Theophylline release rates were determined by ultraviolet light at 271 nm. (USP Method 2, pH 4, 5 phosphate buffer, 37° C., 75 rpm). Data for pellets cured under the comparative high humidity (80% Relative Humidity) heat treatment are reported in Tables 5 and 6.

TABLE 3

Drug Release of 4% Coated Theophylline Pellets (dry cure, 60° C.)
Cure conditions for coated pellets

| Sample | Uncured | 3-1 | 3-2 |
|---|---|---|---|
| Cure time |  | 1 Day | 2 Days |
| Temp. |  | 60° C. | 60° C. |
| Humidity |  | Dry | Dry |

| time | Mean Percent Release ± S.D. (n = 3) | | |
|---|---|---|---|
| 1 hr | 4 | 1 | 1 |
| 2 hr | 9 ± 0.6 | 2 | 2 |
| 4 hr | 17 ± 0.6 | 3 ± 0.6 | 3 |
| 8 hr | 29 ± 0.6 | 6 | 6 |
| 12 hr | 38 ± 0.6 | 8 | 8 ± 0.6 |
| Infinity (200 rpm/ 2 Hrs) | 44 ± 1.0 | 9 ± 0.6 | 9 ± 1.0 |

TABLE 4

Drug Release Testing of 4% Coated Theophylline Pellets
(dry cure, 80° C.)
Cure conditions for coated pellets

| Sample | Uncured | 4-1 | 4-2 |
|---|---|---|---|
| Cure time |  | 1 Day | 2 Days |
| Temp |  | 80° C. | 80° C. |
| Humidity |  | Dry | Dry |

| Time | Mean Percent Release ± S.D. (n = 3) | | |
|---|---|---|---|
| 1 hr | 4 | 1 | 1 |
| 2 hr | 9 ± 0.6 | 2 | 1 ± 0.6 |
| 4 hr | 17 ± 0.6 | 3 | 3 ± 0.6 |
| 8 hr | 29 ± 0.6 | 5 ± 0.6 | 5 |
| 12 hr | 38 ± 0.6 | 7 ± 0.6 | 7 ± 0.6 |
| Infinity (200 rpm/ 2 Hrs) | 44 ± 1.0 | 9 | 9 ± 0.6 |

TABLE 5

Drug Release Testing of 4% Coated Theophylline Pellets
(80% RH, 60° C.)
Cure conditions for coated pellets

| Sample | Uncured | 5-1 | 5-2 |
|---|---|---|---|
| Cure time | 0 | 1 Day | 2 Days |
| Temp |  | 60° C. | 60° C. |
| Humidity |  | 80% RH | 80% RH |

TABLE 5-continued

| Time | Mean Percent Release ± S.D. (n = 3) | | |
|---|---|---|---|
| 1 hr | 4 | 6 ± 0.6 | 6 ± 1.0 |
| 2 hr | 9 ± 0.6 | 10 ± 0.6 | 11 ± 1.5 |
| 4 hr | 17 ± 0.6 | 17 ± 1.2 | 19 ± 2.0 |
| 8 hr | 29 ± 0.6 | 28 ± 1.5 | 29 ± 2.5 |
| 12 hr | 38 ± 0.6 | 34 ± 1.7 | 36 ± 2.1 |
| Infinity (200 rpm/ 2 Hrs) | 44 ± 1.0 | 38 ± 2.1 | 40 ± 2.1 |

TABLE 6

Drug Release Testing of 4% Coated Theophylline Pellets (80% RH, 80° C. cure)
Cure conditions for coated pellets

| Sample | Uncured | 6-1 | 6-2 |
|---|---|---|---|
| Cure | | 1 Days | 2 Days |
| Temp | | 80 C. | 80 C. |
| Humidity | | 80% | 80% RH |

| Time | Mean Percent Release ± S.D. (n = 3) | | |
|---|---|---|---|
| 1 hr | 4 | 14 ± 0.6 | 25 |
| 2 hr | 9 ± 0.6 | 29 ± 1.0 | 43 ± 1.7 |
| 4 hr | 17 ± 0.6 | 47 ± 1.2 | 60 ± 3.2 |
| 8 hr | 29 ± 0.6 | 63 ± 1.2 | 74 ± 2.1 |
| 12 hr | 38 ± 0.6 | 71 ± 1.2 | 80 ± 1.5 |
| Infinity (200 rpm/ 2 Hrs) | 44 ± 1.0 | 76 ± 1.0 | 83 ± 1.5 |

Coalescence is complete after 24 hours at 60° C. as shown by the lack of effect of a further 24 hours of curing (2 days) or dry curing at a higher temperature 80° C.

There was no significant difference in the profiles of pellets cured at 60° C./80% RH versus uncured. Not only did wet curing fail to drive coalescence to completion (as shown by the dry curing results) but also proved counterproductive at 80° C.

80° C./80% RH curing actually increased the release rate versus uncured, the damage to coating barrier integrity being time dependent.

Example 2

The 15% solids aqueous coating dispersion from Table 1 was applied to the pellets as in Example 1 but only up to a 2.0% weight gain under high humidity conditions as shown in Table 7.

TABLE 7

Coating conditions with Niro Fluid Bed Dryer MP-1 with Wurster Column

| Inlet Temperature | 60° C. |
|---|---|
| Air Flow | 60 m³/hr |
| Atomization Pressure | 1 Bar |
| Spray Rate | Masterflex Pump speed setting 15 |
| % RH in Bowl | High humidity: chiller and humidifier off |
| Weight Gain | 2.0% |
| Coating time | 10 min |

The coated pellets were divided and heat treated in a closed oven without air circulation under two different conditions:
1) 60° C. dry
2) 60° C. 80% Relative Humidity (RH)

The dry humidity samples were dried in an open container without active humidity control in a closed oven. The 80% humidity samples were oven dried in a closed container where the humidity was controlled using a saturated salt solution (KCl). Data for pellets cured under dry conditions are reported in Table 8 and illustrate the present invention. Theophylline release rates were determined by ultraviolet light at 271 nm. (USP Method 2, pH 4.5, phosphate buffer, 37° C., 75 rpm). Data for pellets cured under comparative high humidity (80% RH) heat treatment are reported in Table 9.

TABLE 8

Drug Release Testing of 2% Coated Theophylline Pellets (Dry, 60° C. cure)
Cure conditions for coated pellets

| Sample | Uncured | 8-1 | 8-2 |
|---|---|---|---|
| Cure time | | 1 Day | 2 Days |
| Temp | | 60° C. | 60° C. |
| Humidity | | Dry | Dry |

| Time | Mean Percent Release ± S.D. (n = 3) | | |
|---|---|---|---|
| 1 hr | 90 ± 0.6 | 11 ± 1.5 | 9 ± 1.2 |
| 2 hr | 99 ± 1.0 | 20 ± 2.1 | 17 ± 1.5 |
| 4 hr | 100 ± 1.0 | 28 ± 1.5 | 26 ± 2.1 |
| 8 hr | | 37 ± 1.5 | 35 ± 2.6 |
| 12 hr | | 43 ± 1.7 | 41 ± 3.1 |
| Infinity (200 rpm/ 2 Hrs) | | 46 ± 1.7 | 44 ± 2.6 |

TABLE 9

Drug Release Testing of 2% Coated Theophylline Pellets (80% RH, 60° C. cure)
Cure conditions for coated pellets

| Sample | Uncured | 9-1 | 9-2 |
|---|---|---|---|
| Cure time | | 1 Day | 2 Days |
| Temp | | 60° C. | 60° C. |
| Humidity | | 80% | 80% |

| Time | Mean Percent Release ± S.D. (n = 3) | | |
|---|---|---|---|
| 1 hr | 90 ± 0.6 | 10 ± 1.2 | 10 ± 1.2 |
| 2 hr | 99 ± 1.0 | 17 ± 1.7 | 17 ± 1.7 |
| 4 hr | 100 ± 1.0 | 26 ± 2.1 | 26 ± 0.6 |
| 8 hr | | 39 ± 2.3 | 39 ± 1.0 |
| 12 hr | | 46 ± 2.1 | 47 ± 1.2 |
| Infinity (200 rpm/ 2 Hrs) | | 50 ± 2.1 | 52 ± 1.5 |

When high humidity is maintained during coating the humidity of the curing environment is not important, at least for temperatures up to 60° C.

Example 3

This example uses a dispersion at 10% solids and provides 1.5% weight gain, coated under high humidity conditions.

An aqueous coating dispersion of plasticized ethyl cellulose pseudo-lattices was prepared using the formulation in Table 10 by: (1) adding triethyl citrate to AQUACOAT® ECD-30 (FMC Corp., Philadelphia Pa.) and mixing for one hour at slow speed at approximately 100 to 150 RPM using a propeller mixer with a 3 inch impeller blade and (2) adding deionized water and mixing for an additional 10 minutes.

TABLE 10

| Coating formulation at 10% solids | | |
|---|---|---|
| Ingredient | Weight (%) | Weight (%) of solids |
| AQUACOAT ® ECD-30 ethylcellulose dispersion | 27 | 80 |
| triethyl citrate | 2 | 20 |
| deionized water | 71 | 0 |
| | 100 | 100 |

The coating dispersion was applied to an 800 gram batch size of theophylline pellets (average pellet size 1000 microns, 70% theophylline) according to the coating conditions in Table 11 The coating was conducted in a Niro Fluid Bed Dryer MP-1 with Wurster Column. The coating dispersion was stirred by a magnetic stirrer during spray application. The spray rate was measured by timed decrement of the coating removed from the coating vessel after initially zeroing on a Mettler balance.

TABLE 11

| Coating conditions with Niro Fluid Bed Dryer MP-1 with Wurster Column | |
|---|---|
| Inlet Temperature | 60° C. |
| Air Flow | 60 m³/hr |
| Atomization Pressure | 1 Bar |
| Spray Rate | 15 g/min, Masterflex Pump |
| % RH in Bowl | High humidity (chiller and humidifier on) |
| Weight Gain | 15% |
| Coating time | 10 min |

Heat treatment (curing) of the coated pellets was conducted under dry conditions, i.e. no active humidity control, by oven drying in trays in an oven at 60° C., without air circulation. Data for pellets cured under dry conditions are reported in Table 12 and illustrate the present invention. Theophylline release rates were determined by ultraviolet light at 271 nm. (USP Method 2, pH 4.5 phosphate buffer, 37° C., 75 rpm).

TABLE 12

Drug Release Testing of AQUACOAT ® ECD Ethycellulose Dispersion Coated Theophylline Pellets (1.5% Coating weight, cured at 60° C., dry)

| | Cure conditions for coated pellets | | |
|---|---|---|---|
| Sample | 12-1 | 12-2 | 12-3 |
| Cure Time | 1 Hour | 2 Hours | 24 Hours |
| Temp | 60 C. | 60 C. | 60 C. |
| Humidity | Dry | Dry | Dry |
| Release Time (Hrs) | Mean Percent Release ± S.D. (n = 3) | | |
| 0.5 | 27 ± 1.2 | 25 ± 0.6 | 27 ± 2.1 |
| 1 | 43 ± 1.7 | 40 ± 1.5 | 45 ± 2.6 |
| 2 | 59 ± 2.0 | 55 ± 2.3 | 62 ± 2.0 |
| 3 | 67 ± 2.0 | 62 ± 2.1 | 70 ± 1.5 |
| 4 | 73 ± 1.5 | 68 ± 2.0 | 75 ± 1.5 |
| 6 | 79 ± 1.5 | 75 ± 1.2 | 81 ± 1.5 |
| 8 | 83 ± 1.5 | 79 ± 1.2 | 85 ± 1.0 |
| 10 | 86 ± 1.5 | 82 ± 1.0 | 87 ± 1.5 |
| 12 | 88 ± 1.0 | 85 ± 0.6 | 89 ± 1.5 |
| Infinity (200 rpm/ 2 Hrs) | 90 ± 0.6 | 87 ± 1.0 | 92 ± 1.2 |

A weight gain of 1.5% on the coated pellets led to a non-linear release of 90% theophylline in 12 hours. Curing at 60° C. for 1 hour without humidity control was sufficient to stabilize the release profile when coating was conducted under high humidity conditions, i.e. by humidified inlet air and lowering the solids content of the aqueous coating dispersion, i.e. by diluting the AQUACOAT® ECD ethylcellulose dispersion.

Example 4

This example uses a dispersion at 35% solids and provides 2.0% weight gain, coated under low humidity conditions. Portions of the coated pellets were heat treated under differing conditions and the data for heat treatment under dry conditions in accordance with the present invention are compared with data for a comparative heat treatment under high humidity.

An aqueous coating solution of 35% solids was prepared according to the formulation in Table 13. An aqueous coating dispersion of plasticized ethylcellulose pseudo-lattices was prepared using the formulation in Table 13 by adding triethyl citrate to AQUACOAT® ECD-30 ethylcellulose dispersion (FMC Corp., Philadelphia Pa.) and mixing for one hour at a slow speed at approximately 100 to 150 RPM using a propeller mixer with a 3 inch impeller blade.

TABLE 13

| Coating formulation at 35% solids | | |
|---|---|---|
| Ingredient | Weight (%) | Weight (%) of solids |
| AQUACOAT ® ECD-30 ethylcellulose dispersion | 93 | 80 |
| triethyl citrate | 7 | 20 |
| deionized water | 0 | 0 |
| | 100 | 100 |

The coating dispersion was applied to an 800 gram batch size of theophylline pellets (average pellet size 1000 microns, 70% theophylline) according to the coating conditions in Table 14. The coating was conducted in a Niro Fluid Bed Dryer MP-1 with Wurster column to a weight gain of 2% under high humidity conditions. The coating dispersion was stirred by a magnetic stirrer during spray application. The spray rate was measured by timed decrement of the coating removed from the coating vessel after initially zeroing on a Mettler balance.

TABLE 14

| Coating conditions with Niro Fluid Bed Dryer MP-1 with Wurster Column | |
|---|---|
| Inlet Temperature | 60° C. |
| Air Flow | 60 m³/hr |
| Atomization Pressure | 1 Bar |
| Spray Rate | Masterflex Pump speed setting 15 |
| % RH in Bowl | Low humidity: chiller and humidifier off |
| Weight Gain | 2.0% |
| Coating time | 5 minutes |

The coated pellets were divided and heat treated in a closed oven without air circulation under two different conditions.
1) 60° C. dry
2) 60° C. 80% RH The dry humidity samples were dried in an open container without active humidity control in a closed oven. The 80% humidity samples were oven dried in a closed container where the humidity was controlled using a saturated salt solution (KCl). Theophylline release rates were determined by ultraviolet light at 271 nm. (USP Method 2, pH 4.5 phosphate buffer, 37° C., 75 rpm). Data for pellets cured under dry conditions are reported in Table 15 and illustrate the present invention. Data for pellets cured under comparative high humidity (80% RH) heat treatment are reported in Table 16.

TABLE 15

Drug Release Testing of 2% Coated Theophylline Pellets
Cure conditions for coated pellets

| Sample | Uncured | 15-1 | 15-2 |
|---|---|---|---|
| Cure time |  | 1 Day | 2 Days |
| Temp |  | 60° C. | 60° C. |
| Humidity |  | Dry | Dry |
| Time (Hrs) | Mean Percent Release ± S.D. (n = 3) | | |
| 1 | 98 ± 2.3 | 54 ± 2.0 | 56 ± 2.9 |
| 2 | 99 ± 1.7 | | |
| 4 | 100 ± 2.1 | 82 ± 3.5 | 83 ± 2.3 |
| 8 | | 90 ± 3.5 | 90 ± 1.5 |
| 12 | | 93 ± 2.6 | 93 ± 1.5 |
| Infinity (200 rpm/ 2 Hrs) | | 95 ± 2.3 | 94 ± 1.5 |

TABLE 16

Drug Release Testing of 2% Coated Theophylline Pellets
Cure conditions for coated pellets

| Sample | Uncured | 16-1 | 16-2 |
|---|---|---|---|
| Cure time | 0 | 1 Day | 2 Days |
| Temp |  | 60 C. | 60 C. |
| Humidity |  | 80% RH | 80% RH |
| Time (Hrs) | Mean Percent Release ± S.D. (n = 3) | | |
| 1 | 98 ± 2.3 | 40 ± 0.6 | 38 ± 1.5 |
| 2 | 99 ± 1.7 | 57 ± 1.0 | 54 ± 2.1 |
| 4 | 100 ± 2.1 | 72 ± 0.6 | 67 ± 2.1 |
| 8 | | 83 ± 0.6 | 79 ± 2.1 |
| 12 | | 89 ± 1.0 | 85 ± 2.0 |

High humidity curing is not as effective as high humidity coating followed by dry curing.

Example 5

The 15% solids aqueous coating dispersion from Table 1 was applied to the pellets as in Example 1, but at 1.5% weight gain under high humidity conditions as shown in Table 17.

TABLE 17

| Coating Conditions Niro Fluid Bed Dryer MP-1 with Wurster Column | |
|---|---|
| Inlet Temperature | 60° C. |
| Air Flow | 60 m³/hr |
| Atomization Pressure | 1 Bar |
| Spray Rate | Masterflex Pump speed setting 15 |
| % RH in Bowl | High humidity: chiller and humidifier off |
| Weight Gain | 1.5% |
| Coating time | 10 min |

The coated pellets were divided and heat treated in a closed oven without air circulation under two different conditions:
1) 60° C. dry
2) 60° C. 80% Relative Humidity (RH)

The dry humidity samples were dried in an open container without active humidity control in a closed oven. The 80% humidity samples were oven dried in a closed container where the humidity was controlled using a saturated salt solution (KCl). The staged cured samples (80% RH/1 day plus Dry/1 Day) were oven dried first in the closed container with saturated salt solution (KCL) followed by a second stage of drying in an open container without active humidity control. Data for pellets cured under dry conditions or with a staged high humidity cure followed by a dry cure are reported in Table 18 and illustrate the present invention. Theophylline release rates were determined by ultraviolet light at 271 nm. (USP Method 2, pH 4.5, phosphate buffer, 37° C., 75 rpm). Data for pellets cured under high humidity (80% RH) heat treatment are reported in Table 18.

TABLE 18

Drug Release Testing of 1.5% Coated Theophylline Pellets

| Temp | Uncured | 60° C. Dry | 60° C. Dry | 60° C. 80% RH | 60° C. 80% RH | 60° C. 80% RH/1 Day plus Dry/1 Day |
|---|---|---|---|---|---|---|
| Cure time | | 1 day | 2 days | 1 day | 2 days | 2 days |
| Time (Hrs) | Mean Percent Release ± S.D. (n = 3) | | | | | |
| 0.5 | 67 ± 2.6 | 5 | 6 ± 0.6 | 10 ± 1.2 | 9 ± 0.6 | 6 ± 0.6 |
| 1 | 92 ± 1.5 | 10 | 11 ± 0.6 | 17 ± 1.5 | 17 ± 1.5 | 10 ± 1.2 |
| 2 | 97 | 18 ± 0.6 | 19 ± 0.6 | 26 ± 2.5 | 27 ± 2.1 | 18 ± 1.5 |
| 3 | 97 ± 0.6 | 24 ± 1.0 | 24 ± 1.5 | 33 ± 2.5 | 34 ± 2.5 | 24 ± 1.5 |
| 4 | 98 ± 0.6 | 29 ± 0.6 | 28 ± 1.5 | 39 ± 2.6 | 41 ± 3.1 | 29 ± 1.5 |
| 6 | 99 ± 0.6 | 35 ± 1.0 | 35 ± 2.0 | 49 ± 2.6 | 51 ± 3.1 | 37 ± 2.0 |
| 8 | 99 ± 0.6 | 40 ± 1.0 | 40 ± 2.0 | 56 ± 2.1 | 58 ± 3.1 | 43 ± 2.0 |

TABLE 18-continued

| Drug Release Testing of 1.5% Coated Theophylline Pellets | | | | | | |
|---|---|---|---|---|---|---|
| 10 | 99 ± 0.6 | 44 ± 1.0 | 44 ± 2.5 | 61 ± 1.7 | 64 ± 3.2 | 48 ± 2.1 |
| 12 | 99 ± 0.6 | 47 ± 1.0 | 47 ± 2.5 | 66 ± 2.1 | 68 ± 2.6 | 52 ± 2.1 |

Example 6

The 15% solids aqueous coating dispersion from Table 18 was applied to the pellets of Example 1, but to a 1.5% weight gain under high humidity conditions as shown in Table 19.

TABLE 19

| Coating conditions for Niro Fluid Bed Dryer MP-1 with Wurster Column | |
|---|---|
| Inlet Temperature | 60° C. |
| Air Flow | 60 m³/hr |
| Atomization Pressure | 1 Bar |
| Spray Rate | Mastertflex Pump speed setting 15 |
| % RH in Bowl | High humidity: chiller and humidifier off |
| Weight Gain | 1.5% |
| Coating time | 10 min |

The coated pellets were divided and heat treated in a closed oven without air circulation at 60° C. dry for 1 hour.

The dry humidity samples were dried in an open container without active humidity control in a closed oven. Data for pellets cured under dry conditions are reported in Table 20 and illustrate the present invention. The cured pellets were stored in a closed container under 40° C./75% RH for a stability test. Theophylline release rates were determined by ultraviolet light at 271 nm. (USP Method 2, pH 4.5, phosphate buffer, 37° C., 75 rpm). Data are reported in Table 20.

TABLE 20

| Drug Release Testing of 1.5% Coated Theophylline Pellets after 40° C./75% RH Storage | | | | |
|---|---|---|---|---|
| Time (Hrs) | Initial | 4 Weeks | 8 Weeks | 12 Weeks |
| 0.5 | 34 ± 1.5 | 38 ± 0.6 | 41 ± 2.5 | 32 ± 1.2 |
| 1 | 55 ± 2.3 | 61 ± 0.6 | 64 ± 2.0 | 51 ± 1.5 |
| 2 | 73 ± 1.5 | 79 ± 0.6 | 80 ± 1.5 | 69 ± 1.5 |
| 3 | 81 ± 1.7 | 86 ± 0.6 | 87 ± 1.0 | 77 ± 1.5 |
| 4 | 85 ± 1.5 | 90 ± 0.6 | 90 ± 1.0 | 81 ± 2.1 |
| 6 | 91 ± 2.1 | 93 ± 1.5 | 94 ± 0.6 | 87 ± 2.1 |
| 8 | 93 ± 1.7 | 95 ± 1.2 | 96 ± 0.6 | 90 ± 2.1 |
| 10 | 95 ± 2.1 | 97 ± 1.7 | 97 ± 0.6 | 92 ± 2.0 |
| 12 | 96 ± 2.0 | 98 ± 1.5 | 98 ± 1.0 | 93 ± 2.0 |

Example 7

Using a 15% aqueous dispersion of AQUACOAT® ECD ethylcellulose dispersion (FMC Corp.) plasticized with 24% triethyl citrate (TEC) coating loadings of 1.5% to 4% by weight were applied to 800 grams of 1 mm diameter theophylline pellets using a Niro MP-1 fluid bed with a Wurster insert. High humidity was maintained by steam bleed to the inlet air. Coated pellets were dry cured by oven drying in trays. For wet curing at the same temperatures, the pellets were placed above saturated aqueous potassium chloride slurries in sealed containers. Theophylline release rates were determined by ultraviolet light at 271 nm. (USP Method 2, pH 4.5 phosphate buffer, 37° C., 75 rpm.) The release profiles of pellets coated with a 4% coating loading under high humidity and cured under various conditions are shown in FIG. 1.

Figure 3:
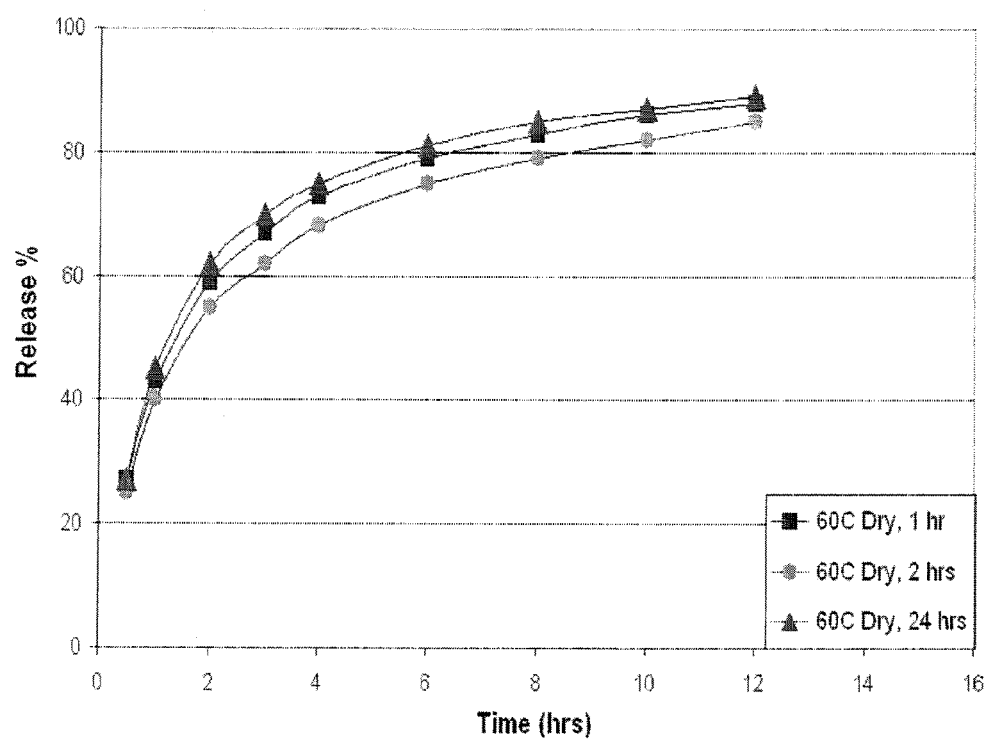
FIG. 3 shows the effect of curing time on theophylline release from coated pellets (high humidity, 1.5% coating weight gain).

Coalescence is complete after 24 hours at 60° C. as shown by the lack of effect of a further 24-hour curing (2 days) or dry curing at a higher temperature 80° C. An extended curing time was deliberately used to ensure a fully coalesced film, and as shown in FIG. 3, shorter curing times may be used in practice.

There was no significant difference in the profiles of pellets cured at 60° C./80% RH versus uncured pellets. Not only did wet curing fail to drive coalescence to completion (as shown by the dry curing results), but it also proved counterproductive at 80° C.

80° C./80% RH curing actually increased the release rate versus uncured, the damage to coating barrier integrity being time dependent.

Figure 2:
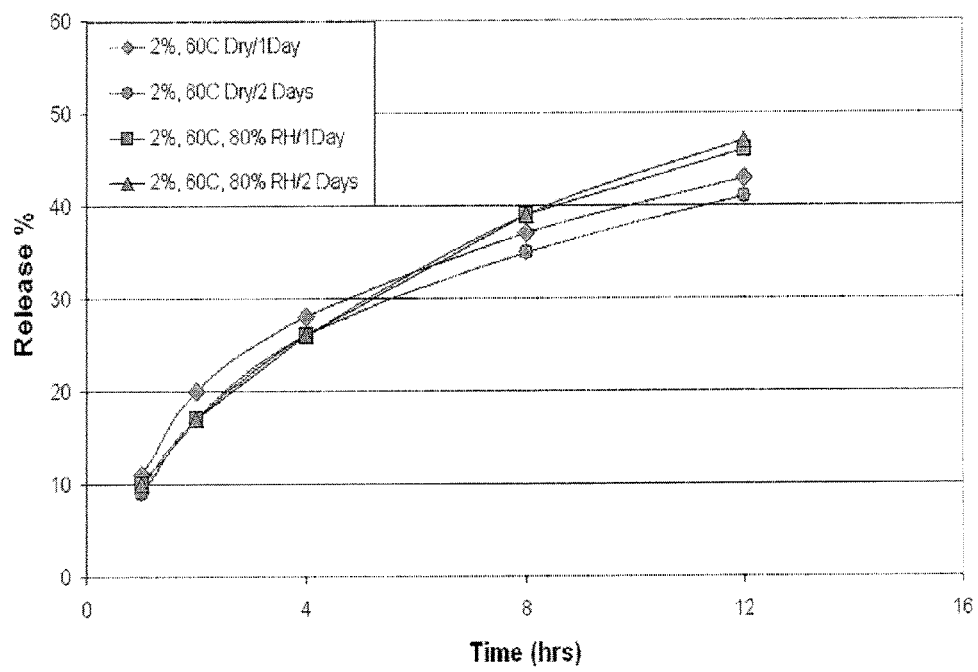
FIG. 2 shows the lack of effect of humidity during curing on release from coated pellets (high-humidity coating 2% coating weight gain).

When high humidity is maintained during coating, the humidity of the curing environment is not important, at least for temperatures up to 60° C., as shown in FIG. 2.

As can be seen from FIG. 3, a one-hour curing time is adequate to stabilize the release profile.

From this example, it can be concluded that high-humidity coating conditions are beneficial and can be created by low dispersion solids, as well as active humidity control.

Dry curing is effective for stabilizing the coated pellets, contrary to claims that high-humidity curing is more effective.

Ensuring full coalescence gives more stable release profiles and allows use of lower coating loadings.

It is to be understood that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed

What is claimed is:

1. A process for coating a substrate with an aqueous polymer coating composition comprising the steps of:
   (i) coating said substrate with said aqueous polymer coating composition under a high relative humidity of greater than 40% followed by,
   (ii) a heat treatment step; wherein said heat treatment step is conducted under low humidity conditions of less than 16 grams of water/kg of air, and said aqueous polymer coating composition comprises a latex or pseudolatex film former comprising ethylcellulose.

2. The process of claim 1, wherein the aqueous polymer coating composition further comprises a plasticizer.

3. The process of claim 2, wherein said high humidity is greater than 50% relative humidity.

4. The process of claim 2, wherein said high humidity is greater than 60% relative humidity.

5. The process of claim 2, wherein said high humidity is greater than 70% relative humidity.

6. The process of claim 2, wherein said high humidity is greater than 80% relative humidity.

7. The process of claim 2, wherein said high humidity is greater than 90% relative humidity.

8. The process of claim 2, wherein said low humidity is less than 10 grams of water/kg of air.

9. The process of claim 2, wherein said low humidity is less than 8 grams of water/kg of air.

10. The process of claim 2, wherein said low humidity is less than 5 grams of water/kg of air.

11. The process of claim 2, wherein said low humidity is less than 3 grams of water/kg of air.

12. The process of claim 2, wherein said heat treatment step is conducted at a temperature above a minimum film forming temperature of said aqueous polymer coating composition.

13. The process of claim 2, wherein said heat treatment step is conducted at a temperature above 40° C.

14. The process of claim 2, wherein said heat treatment step is conducted at a temperature above 60° C.

15. The process of claim 2, wherein said heat treatment step is conducted at a temperature above 80° C.

16. The process of claim 2, wherein said heat treatment step is conducted at a temperature above 90° C.

17. The process of claim 2, where said high humidity in step (i) is maintained by humidification of process air.

18. The process of claim 2, where said high humidity in step (i) is maintained by spraying an aqueous solution into a coating chamber comprising the substrate.

19. The process of claim 2, where said high humidity in step (i) is maintained by diluting the aqueous polymer coating composition with an aqueous solution.

20. The process of claim 2, wherein said polymer coating composition is present on the substrate in an amount less than 8% by weight of said substrate after the heat treatment step.

21. The process of claim 2, wherein said polymer coating composition is present on the substrate in an amount less than 6% by weight of said substrate after the heat treatment step.

22. The process of claim 2, wherein said polymer coating composition is present on the substrate in an amount less than 4% by weight of said substrate after the heat treatment step.

23. The process of claim 2, wherein said polymer coating composition is present on the substrate in an amount less than 2% by weight of said substrate after the heat treatment step.

24. The process of claim 2, wherein said polymer coating composition is present on the substrate in an amount less than 1.5% by weight of said substrate after the heat treatment step.

25. The process of claim 2, wherein said polymer coating composition is present on the substrate in an amount less than 1% by weight of said substrate after the heat treatment step.

26. The process of claim 2, wherein said polymer coating composition is present on the substrate in an amount less than 0.5% by weight of said substrate after the heat treatment step.

27. The process of claim 2, wherein said substrate is selected from the group consisting of a pellet, a tablet, a soft capsule, a hard capsule, a powder, a granules, a bead, a film and a film-enrobed dosage form.

28. The process of claim 2, wherein said high humidity condition is created by said aqueous polymer coating composition having a low solids content of 15% or less.

\* \* \* \* \*